United States Patent [19]
Forsythe et al.

[11] Patent Number: 6,010,728
[45] Date of Patent: *Jan. 4, 2000

[54] PROCESS FOR PROMOTING SKIN HEALING OF FRESHLY DUG POTATOES

[76] Inventors: Darol Forsythe, 15401 Cartwright Rd., Boise, Id. 83703; John M. Forsythe, 4277 Balivi La., Nampa, Id. 83687

[ * ] Notice: This patent issued on a continued prosecution application filed under 37 CFR 1.53(d), and is subject to the twenty year patent term provisions of 35 U.S.C. 154(a)(2).

[21] Appl. No.: 08/887,545

[22] Filed: Jul. 3, 1997

Related U.S. Application Data

[63] Continuation-in-part of application No. 08/570,255, Dec. 11, 1995, abandoned, and a continuation-in-part of application No. 08/175,620, Dec. 30, 1993, abandoned, and a continuation-in-part of application No. 08/133,453, Oct. 7, 1993, abandoned.

[51] Int. Cl.$^7$ ............................... A23B 9/16; A23L 3/34
[52] U.S. Cl. ...................... 426/302; 426/309; 426/310; 426/442
[58] Field of Search ................... 426/312, 442, 426/443, 310, 302, 321, 309; 504/327, 253

[56] References Cited

U.S. PATENT DOCUMENTS

| | | | |
|---|---|---|---|
| 3,742,094 | 6/1973 | Kishino et al. | 260/940 |
| 4,078,480 | 3/1978 | Luck | 99/476 |
| 5,244,866 | 9/1993 | Tayler | 504/253 |
| 5,622,912 | 4/1997 | Riggle et al. | 504/143 |
| 5,918,537 | 7/1999 | Forsythe et al. | 99/467 |

OTHER PUBLICATIONS

Lewis et al., "Dimethylnaphthalene and Diisopropylnaphthalene for Potato Sprout Control in Storage: I. Application, Methodology and Efficacy", American Potato Journal, vol. 74, pp. 183 and 194, 1997.

Glynn et al., U.S.D.A. article entitled "Title of Harvest in Key in Controlling Tuber Damage", Valley Potato Grower, p. 27, Jul. 1995.

Lulal, U.S.D.A. article entitled "Research Leads to More Hastened Skin–Set", Valley Potato Grower, p. 28, Jul. 1995.

Dainello et al., "Chemical Induction of Suberization in Cut Potato Seed Pieces", Journal of the American Society for Horticultural Science, vol. 96 (2), pp. 194–195, Mar. 1971.

Beveridge et al., "Dimethylnaphthalene as a sprout suppressant for seed and ware potatoes", Potato Res. 24, pp. 77–88, 1981.

*Primary Examiner*—Milton Cano
*Attorney, Agent, or Firm*—Trask, Britt & Rossa

[57] ABSTRACT

A method to promote skin healing of freshly dug potatoes is disclosed. Treatment of freshly dug potatoes with DMN either prior to or immediately after storage promotes rapid healing of cuts, abrasions and similar injuries to the potatoes. Liquid DMN may be sprayed on freshly dug potatoes in the field immediately after being dug, during transport from the field, while being conveyed into a storage facility or immediately after being stored. Once in a storage facility, the potatoes may also be treated with a vapor or mist of DMN either in addition to initial treatments or instead of earlier treatments. Further, such DMN treated potatoes may be stored under low humidity conditions without significant dehydration or softening. Stored potatoes first treated with DMN may be later advantageously treated with low levels of CIPC for effective sprout inhibition.

13 Claims, 1 Drawing Sheet

PROCESS FOR PROMOTING SKIN HEALING OF FRESHLY DUG POTATOES

RELATED APPLICATIONS

This application is a continuation-in-part of application Ser. No. 08/570,255 filed Dec. 11, 1995, now abandoned, which is continuation-in-part of application Ser. No. 08/175,620, filed Dec. 30, 1993, now abandoned, which is continuation-in-part of application Ser. No. 08/133,453, filed Oct. 7, 1993, now abandoned, the contents of which are incorporated herein by reference.

BACKGROUND OF THE INVENTION

1. Field of the Invention

This invention relates to methods and compositions for treating freshly dug potatoes.

2. State of the Art

Potatoes, when being dug are frequently bruised, cut and/or abraded. These injuries to the potatoes oftentimes cause spoilage during shipment, storage and the like. A process known as suberization occurs naturally which tends to heal many of these injuries. However, whenever potatoes are stored, which occurs with a particularly large portion of potatoes harvested in any given year, if healing occurs slowly a significant loss of potatoes can occur through spoilage.

For example, it is relatively common in the potato storage industry to treat potatoes with Chloroisopropyl-N-carbamate (CIPC) to prevent or retard development of sprouts in the potatoes. Even though potatoes are stored at a cool temperature, for example, generally between about 40° and 45° F., sprouting does begin to occur after a couple months of storage. Storage of upwards of six to eight months is typical for a stored potato harvest. Thus, without treatment of a chemical such as CIPC, the stored potatoes become entangled in sprouts and the whole stored lot of potatoes may become economically useless. Although early treatment with CIPC could be advantageous for sprout inhibition purposes, application of CIPC is typically delayed until after suberization has occurred inasmuch as CIPC tends to retard suberization, resulting in accelerated rot and spoilage.

BRIEF SUMMARY OF THE INVENTION

A method and composition for treating freshly dug potatoes to promote healing has now been discovered. The method generally involves applying to the potatoes at least small quantities of one or more isomers of dimethyl-naphthalene (hereinafter DMN), preferably as promptly after the potatoes are dug as possible, including treatment in the field, treatment during transportation and early treatment in a storage facility. The treatment process may include spraying a concentrated or dilute liquid solution or suspension of DMN onto potatoes immediately after harvesting or during transport or during the early stages of storage to promote the suberization process. Also, once potatoes are placed in a storage facility, the DMN may be applied as a mist or as a vapor. Generally it is desired to have sufficient DMN applied to the potatoes so that at least some DMN is in contact with the injured portion of the potato.

BRIEF DESCRIPTION OF THE DRAWING(S)

FIG. 1 shows a graph illustrating the protocol for treating stored potatoes.

DETAILED DESCRIPTION OF THE INVENTION

Figure 1:
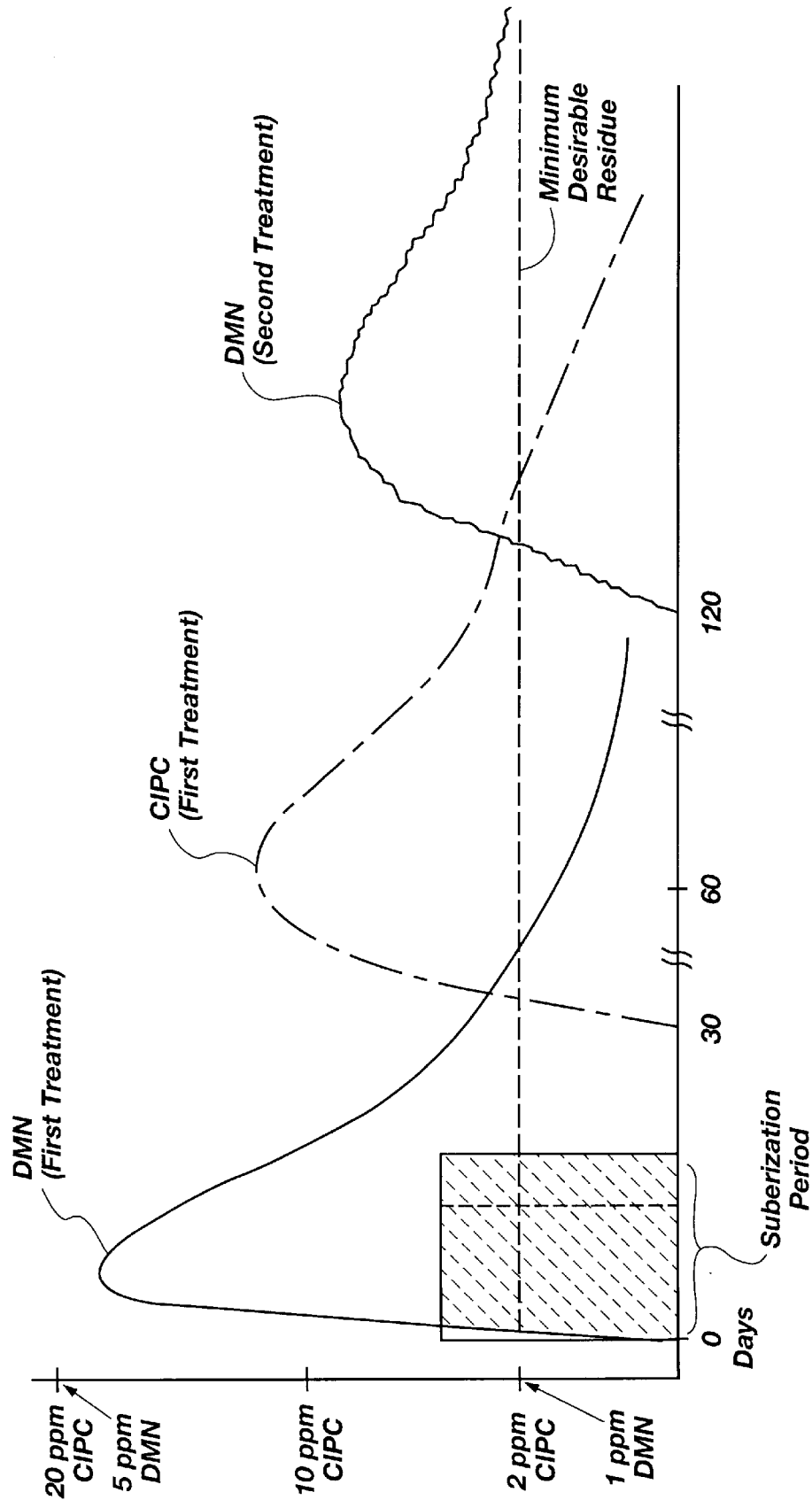

The instant invention relates to a method and composition for promoting the healing of freshly dug potatoes. Potatoes during the digging process are often cut, scraped, abraded and injured in various ways. If potatoes are used immediately after being harvested, then these injuries present no problem whatsoever. However, since most potatoes produced commercially are stored for various periods of times, sometimes up to almost a year, the damaged potato tissue is more susceptible to rot, mold, fungi, infestation by insects and like. Wile potatoes go through a natural "healing" process called suberization wherein the chemical suberin is formed to convert cell tissue into a corky-like protective layer similar to a callous, this suberization process requires some period of time and often some significant spoilage from rot, infection, insect infestation and the like begins prior to the completion of the suberization process. Once these deterioration mechanisms have begun, the likelihood of ultimate spoilage is very great.

Since potatoes which are produced commercially are stored for lengthy periods of time, it is necessary to treat those potatoes to prevent sprout growth during storage which can destroy the economic value of the stored potatoes. Generally, it has been the practice to delay any application of sprout inhibitors such as CIPC until the suberization process has been completed. Application of CIPC, which is currently the most commonly applied sprout inhibitor, is relatively effective as a sprout inhibitor even with delay in application associated with the suberization process. It would be desirable, however, if the application of a sprout inhibitor could be initiated at an earlier stage during the storage process. The suberization process, depending upon the type of potato, humidity, temperature and other conditions, usually requires from several days to several weeks after the potatoes are dug in order for this natural "healing" process to be completed.

The instant invention involves a process and composition whereby freshly dug potatoes may be treated to promote the healing or suberization process. The invention comprises the application of small quantities of one or more of the isomers of dimethyl-naphthalene (DMN) to the potatoes relatively soon after the potatoes are dug. Since dimethyl-naphthalene is a liquid regardless of which isomer is utilized, although the 1,4isomer is generally preferred, a concentrated form of DMN may be applied to the potatoes. The DMN may be applied by immersing the potatoes in a bath of DMN or DMN may be sprayed upon the potatoes or once the potatoes are in a storage facility, the DMN may be applied as a vapor or as a mist. Also, since only very minute quantities of DMN are required in order to promote effectively the potato healing process, DMN may be present in a minor amount in a solution, suspension or an emulsion.

After early treatment with DMN, potatoes so treated may advantageously be treated subsequently with CIPC or other conventional sprout inhibitor.

It is known that DMN is present in potatoes and there have been prior suggestions regarding use of DMN as a sprout inhibitor, for example, in the hereinabove related parent application. Also, certain literature has suggested that the concentration of DMN in the atmosphere surrounding stored potatoes be monitored and when it drops to a certain level that DMN then be added to the atmosphere of the stored facility on a continuous or semi-continuous basis to retain a certain level of DMN in the atmosphere surrounding the potatoes. This latter literature suggestion contemplates a significant delay in treatment with DMN after harvested potatoes have been stored and well after the natural suberization process would have been completed.

The early application of DMN for different purposes than sprout inhibitation has not been heretofore suggested. In the aforementioned parent application, it is suggested that DMN be applied in early stages of storage as a sprout inhibitor. However, as described in other literature, the late treatment of potatoes with DMN would not be effective for the promotion of suberization since the potatoes would have already naturally healed or would have already begun to experience deterioration by way of rot, mold, fungi, insect infestation and the like.

In a preferred embodiment of the instant invention, potatoes are treated with DMN within about forty-eight hours of being harvested. The potatoes at that time may already be in a storage facility and may be treated in the various ways described herein. Effective treatment with DMN at such an early stage promotes rapid healing of the potatoes and thus permits, if desired, earlier applications of a sprout inhibitor. Also, since DMN possesses sprout inhibitation characteristics, the early treatment of potatoes with DMN tends to increase the amount of DMN in the skin and surface layers of the potato and tends to delay sprouting so that such an early application of DMN may accomplish more than the mere healing of injured potatoes.

There are a number of convenient events during the harvesting and storing of potatoes during which DMN may be readily applied. For example, harvested potatoes are generally fed by a conveyor into trucks so that the potatoes may be hauled to storage facilities. The trucks may be equipped with a spray so that as the potatoes are conveyed into the truck, the potatoes may be sprayed on the conveyor or the potatoes may be sprayed as they are entering the truck bed. Also, potatoes are conveyed from the truck to the storage facility and may be sprayed during this conveying process with liquid DMN in either concentrated or dilute form as a solution, suspension or emulsion. Also, it may be convenient that upon filling of a storage facility, which usually is begun within 24 hours of harvest, to seal the storage facility and treat the potatoes with a vapor or mist of DMN. Very large storage facilities may require a week or more to be filled, thus treatment of the potatoes prior to sealing the facility is very desirable.

During this initial storage period, it is typical to cool the stored potatoes since the potatoes begin to respire, which involves heat generation, and are relatively warm from the ground. Long term storage is typically carried out at about 40° to 45° F. Usually it is not difficult to maintain this temperature in potato growing regions such as Idaho, Washington, Oregon, Maine and other large potato growing regions in the United States and throughout the world. These regions tend to be in temperate climates where the storage season occurs during winter and cool outside air may be introduced to maintain a low temperature storage condition. During harvesting, however, the temperatures may not be sufficiently cool and the introduction of a mist of DMN may assist in cooling the air in a potato storage facility to offset some of the heat contained by the freshly dug potatoes and being generated by respiration of the potatoes. Also, it is typical to maintain a relatively high humidity condition for example, about 95% moisture in the air during the storage of potatoes. Thus, the combination of misting water and DMN either as a mixture or jointly evaporated materials may be desirable to promote healing and to control temperature. Generally, healing proceeds better in relatively high humidity conditions.

In experiments conducted with early treatment of potatoes with DMN, it was generally noted that the DMN treated potatoes underwent the suberization process approximately twice as fast as untreated potatoes. The following example demonstrates the effectiveness of the 1,4-isomer of DMN in promoting the healing process of freshly dug potatoes.

A pile of freshly dug potatoes having considerable injuries such as cuts, scrapes and abrasions were sprayed with pure 1,4-dimethyl naphthalene. The pile was located outdoors with a humidity condition of about 40%. Within about two days after spraying, the suberization processes appeared to be complete with only a small portion of the injured potatoes showing any evidence of rot. Although a control sample wasn't used, potatoes with such a large quantity of cuts, abrasions and the like in an exposed, low humidity environment would typically show minimal healing and a considerable amount of rot.

The healing process for injured potatoes appeared to proceed about twice as fast for freshly dug potatoes treated with DMN in comparison to untreated potatoes. Also, the DMN treatment appeared to interrupt the rotting process inasmuch as potatoes showing some signs of spoilage when treated did not show increased rot when inspected periodically over a several week period.

It is not known to what extent DMN and other volatile chemicals found in and near the skin of a potato play a role in the suberization process. Thus, the chemical effect of the instant invention is not fully understood. However, after repeated treatment of injured, freshly dug potatoes, it has been noted that the potatoes healed much more rapidly when treated with DMN than when similarly injured potatoes were not so treated.

Although treatment of injured potatoes with DMN promotes healing in low humidity, high temperature environments, the healing process proceeds most rapidly if the potatoes are exposed during treatment or shortly thereafter to a high humidity, low temperature environment. This is very important for potatoes which are known to undergo a suberization very slowly. The Russet Burbank potato undergoes relatively fast suberization even without DMN treatment and proceeds to heal extremely quickly when subjected to DMN treatment even at low humidity and high temperature conditions.

Thus, for slow healing potatoes it is desirable to treat the potatoes with DMN as quickly as possible after the potatoes are dug and expose them to a high humidity, cool environment as quickly as possible.

As indicated hereinabove, DMN may be applied in a pure form as a liquid spray, as a mist or as a vapor. In diluted form, DMN may be present in a solvent, preferably one which is non-toxic, although even toxic solvents can be used since the treatment is done early and the solvent will completely evaporate by the time stored potatoes are sent to the market.

An aqueous mixture of DMN may also be advantageously applied as a spray, mist or vapor. Water and DMN are immersible, however, vigorous agitation may maintain a substantially evenly distributed suspension of DMN in water. The mixing may be conducted in a tank as in a mixing chamber of a spray or misting machine. Generally, it is preferred that DMN be present with at least 5%, although preferably 10%, by volume of any suspension or solution.

Vaporization of DMN in a substantially sealed environment, e.q., a storage facility or a treatment unit is an effective way of treating potatoes to promote suberization.

Freshly dug potatoes destined for market rather than storage may be treated by spraying or misting in an open environment or by vapors in a sealed environment. Even fresh potatoes which go directly to market may experience considerable spoilage if suberization does not occur promptly. Thus, because DMN is non-toxic, even potatoes destined for immediate sale may be advantageously treated with DMN.

Most potatoes destined for immediate sale are roughly sized, sorted, washed and then boxed or bagged. The sizing is generally conducted automatically by sizing machines. Sorting is often done by hand whereby badly damaged or rotten potatoes are removed from conveyors. Washing is done either in batchwise manner or continuously. The wash water may advantageously contain suspended DMN. The potatoes are then allowed to dry and are later packaged.

EXAMPLE

Potatoes which had been freshly harvested were treated with DMN upon being placed in a storage facility. The potatoes had not completed suberization and contained cuts and bruises. The DMN was applied at a dosage rate which provided an effective initial DMN residue on the potatoes of about 2 to 5 ppm.

It was observed, upon removal of samples of potatoes after suberization had been completed (about 20 days after DMN treatment), that the potatoes had less spoilage than control potatoes which had not received DMN treatment. Also, the suberization process occurred more quickly with the DMN treated potatoes in comparison with untreated controls.

The DMN treated potatoes were later treated with CIPC about 60 days after the DMN treatment. The CIPC was applied at a residue level of about 4 to 10 ppm by thermal fogging.

Later, when the CIPC residue had fallen to an average level of about 2 ppm, a vapor of DMN was introduced to cause a residue level of about 0.5 to about 2 ppm to be deposited on the potatoes.

The graph of FIG. 1 illustrates a desirable protocol for treated stored potatoes.

Initially, e.g. at or near day one in the storage facility or as the potatoes are conveyed into a storage facility, a spray of DMN, preferably 1,4-DMN is applied to provide a residue level of about 2 to 5 ppm. This treatment aids significantly in promoting suberization, healing of cuts, etc., hardness and other desirable characteristics.

Over a period of weeks, the residue level will diminish. Thus, when the residue level reaches an average of about 0.5 to 1.0 ppm of DMN, the potatoes are then fogged with an aerosol of CIPC to place a residue of about 4 to 10 ppm on the potatoes. This treatment may occur typically about 30 to 50 days after the DMN treatment. This CIPC treatment may be effective at lower levels of CIPC residue than would conventionally be applied in the absence of the first DMN treatment.

About 8 to 12 weeks after the CIPC treatment another treatment is done with vapors of DMN (1,4-DMN) for the purpose of maintaining the potatoes in a firm (hard), non-sprouting condition during the remainder of storage and during post-storage shipment and use. A residue of about 2 to 5 ppm is applied.

The second DMN treatment is preferably done when the CIPC residue has dropped to about 2 ppm. This DMN vapor treatment may be conducted with the storage facility sealed for a period of 24 to 48 hours or more. However, this treatment usually occurs some four to five months after storage when outside temperatures are still cool and heat given off by the potatoes will not unduly raise the storage temperature.

It is seen from FIG. 1 that a subsequent treatment with sprout inhibitor occurs before the residue of the previously applied sprout inhibitor falls below the desired minimum, e.g., about 2 ppm for CIPC and about 0.5 ppm for 1,4-DMN.

A further advantage of early treatment with DMN, especially 1,4-DMN, is to minimize the development of silver scruff, a serious potato disease caused by a fungus.

No approved method exists for treating silver scruff. Effective fungicides are not approved for treatment of potatoes. Recently, it has been suggested that silver scruff may be eliminated or minimized if storage is conducted under conditions of low humidity, e.g. 75–85%, rather than 95% plus typically utilized. A disadvantage of low humidity storage is that such potatoes dehydrate and soften. This causes the potatoes to be less acceptable for certain markets and results in some loss of product. It has been discovered, however, that early treatment of such potatoes with 1,4-DMN causes the potatoes to stay hydrated and firm even under storage conditions of 85%, and less, humidity.

Heretofore, treatment of potatoes with DMN has been conducted under desirable storage conditions, that is, humidity of about 95° and temperatures of 42–45° F.

Although various techniques and methods have been described hereinabove, the instant invention is not to be limited thereto, but to be within the scope of the appended claims.

What is claimed is:

1. A method of treating freshly dug potatoes to promote skin healing comprising: applying 1,4 DMN to said freshly dug potatoes.

2. The method of claim 1 wherein said 1,4 DMN is applied to said freshly dug potatoes prior to storage.

3. The method of claim 1 wherein said 1,4 DMN is applied within about two days of being dug.

4. The method of claim 1 wherein said 1,4 DMN is applied substantially immediately after said potatoes are dug.

5. The method of claim 1 wherein said 1,4 DMN is applied to said potatoes substantially immediately after storage.

6. The method of claim 5 wherein said 1,4 DMN is applied as a vapor.

7. The method of claim 5 wherein said 1,4 DMN is applied as a mist.

8. The method of claim 1 wherein said 1,4 DMN is applied as a liquid spray.

9. The method of claim 1 wherein said freshly dug potatoes are in an unwashed condition.

10. The method of claim 1 wherein said 1,4 DMN is in substantially pure form.

11. The method of claim 1 wherein said 1,4 DMN is combined with a diluent to form a 1,4 DMN-diluent combination.

12. The method of claim 11 wherein said 1,4 DMN is present as at least 5% of said 1,4 DMN-diluent combination.

13. A method of minimizing dehydration and softening of potatoes stored under conditions of humidities less than about 85% relative humidity comprising:

treating said potatoes with 1,4 DMN during dormancy to maintain a residue of at least about 0.5 ppm on said potatoes.

* * * * *